(12) United States Patent
Hafner et al.

(10) Patent No.: US 9,556,164 B2
(45) Date of Patent: Jan. 31, 2017

(54) SALTS OF DASATINIB IN CRYSTALLINE FORM

(71) Applicant: BASF SE, Ludwigshafen (DE)

(72) Inventors: Andreas Hafner, Gelterkinder (DE); Fritz Blatter, Reinach (CH); Martin Szelagiewicz, Basel (CH); Bernd Siebenhaar, Kandern-Wollbach (DE); Tiziana Chiodo, Mannheim (DE); Tobias Hintermann, Therwil (CH); Beate Salvador, Ellerstadt (DE); Marcus Vossen, Limburgerhof (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/907,148

(22) PCT Filed: Jul. 22, 2014

(86) PCT No.: PCT/EP2014/065675
§ 371 (c)(1),
(2) Date: Jan. 22, 2016

(87) PCT Pub. No.: WO2015/011120
PCT Pub. Date: Jan. 29, 2015

(65) Prior Publication Data
US 2016/0168143 A1 Jun. 16, 2016

(30) Foreign Application Priority Data
Jul. 25, 2013 (EP) .................................... 13178021

(51) Int. Cl.
*C07D 417/12* (2006.01)
*C07D 275/06* (2006.01)

(52) U.S. Cl.
CPC ........... *C07D 417/12* (2013.01); *C07D 275/06* (2013.01); *C07B 2200/13* (2013.01)

(58) Field of Classification Search
CPC .. C07D 417/12; C07D 275/06; C07B 2200/13
See application file for complete search history.

(56) References Cited

U.S. PATENT DOCUMENTS

| | | | |
|---|---|---|---|
| 6,596,746 B1 | 7/2003 | Das et al. | |
| 7,491,725 B2 | 2/2009 | Lajeunesse et al. | |
| 7,973,045 B2 | 7/2011 | Simo et al. | |
| 8,067,423 B2 | 11/2011 | Simo et al. | |
| 8,796,481 B2 | 8/2014 | Berens et al. | |
| 9,199,997 B2 | 12/2015 | Yamamoto et al. | |
| 9,221,789 B2 | 12/2015 | Chiodo et al. | |
| 9,290,452 B2 | 3/2016 | Hafner et al. | |
| 2004/0054186 A1 | 3/2004 | Das et al. | |
| 2006/0004067 A1 | 1/2006 | Chen et al. | |
| 2014/0205641 A1 | 7/2014 | Sowa et al. | |
| 2015/0126520 A1 | 5/2015 | Chiodo et al. | |
| 2015/0133463 A1 | 5/2015 | Chiodo et al. | |
| 2015/0246901 A1 | 9/2015 | Chiodo et al. | |
| 2015/0333124 A1 | 11/2015 | Hintermann et al. | |
| 2016/0015034 A1 | 1/2016 | Bratz et al. | |

FOREIGN PATENT DOCUMENTS

| | | |
|---|---|---|
| CN | 102030745 A | 4/2011 |
| WO | WO-00/62778 A1 | 10/2000 |
| WO | WO-2007/035874 A1 | 3/2007 |
| WO | WO-2009/053854 A2 | 4/2009 |
| WO | WO-2010/062715 A2 | 6/2010 |
| WO | WO-2010/067374 A2 | 6/2010 |
| WO | WO-2010/081443 A2 | 7/2010 |
| WO | WO-2013/081016 A1 | 6/2013 |

OTHER PUBLICATIONS

U.S. Appl. No. 14/906,974, filed Jan. 22, 2016, Hafner et al.
"Amorphous active pharmaceutical ingredients having special characteristics and methods for their preparation", Research Disclosure, vol. 538, No. 1, pp. 127 (Feb. 1, 2009).
Banerjee, R., et al., "Saccharin Salts of Active Pharmaceutical Ingredients, Their Crystal Structures, and Increased Water Solubilities", Crystal Growth & Design, vol. 5, No. 6, (2005), pp. 2299-2309.
Das, J., et al., "2-aminothiazole as a novel kinase inhibitor template. Structure-activity relationship studies toward the discovery of N-(2-Chloro-6-methylphenyl)-2-[{6-[4-(2-hydroxyethyl)-1-piperazinyl)]-2-methyl-4-pyrimidinyl)]amino)]-1,3-thiazole-5-carboxamide (Dasatinib, BMS-354825) as a Potent pan-Src Kinase Inhibitor", Journal of Medicinal Chemistry, vol. 49, No. 23, pp. 6819-6832 (Nov. 1, 2006).

(Continued)

*Primary Examiner* — Alexander R Pagano
*Assistant Examiner* — Ebenezer O Sackey
(74) *Attorney, Agent, or Firm* — Drinker Biddle & Reath LLP

(57) ABSTRACT

The present invention primarily relates to molecular crystalline substances, preferably salts of Dasatinib in crystalline form, comprising a compound of formula 1, preferably a cation of a compound of formula 1, formula 1

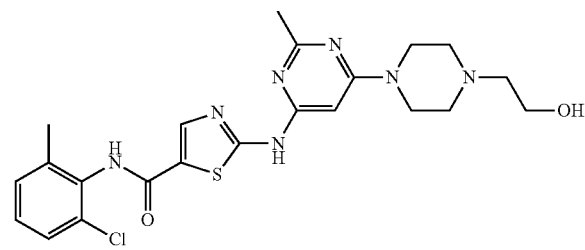

and a second compound selected from the group consisting of glutaric acid, nicotinic acid and saccharin, preferably an anion thereof. The invention is further related to pharmaceutical compositions comprising such a substance. Furthermore, the invention relates to processes for preparing said substances. The invention also relates to several aspects of using said substances or pharmaceutical compositions to treat a disease.

19 Claims, 5 Drawing Sheets

(56) References Cited

OTHER PUBLICATIONS

Figure 1:
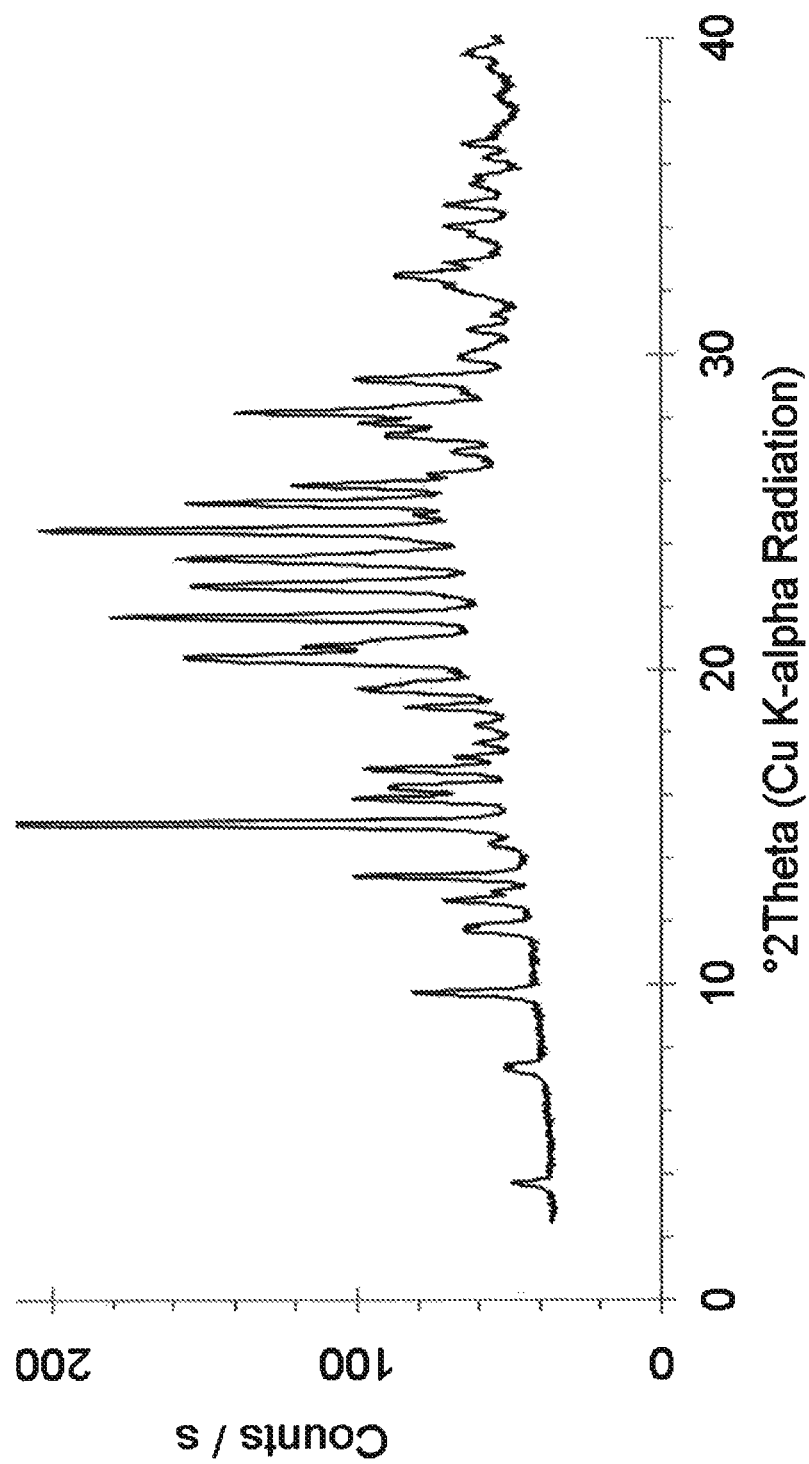

Hancock, B., et al., "Molecular mobility of amorphous pharmaceutical solids below their glass transition temperatures", Pharmaceutical Research, vol. 12, No. 6, (1995), pp. 799-806.
International Search Report for PCT/EP2014/065675 mailed Feb. 16, 2015.
Rodriguez-Spong, B., et al., "General principles of pharmaceutical solid polymorphism: a supramolecular perspective", Advanced Drug Delivery Reviews, vol. 56, No. 3, (2004), pp. 241-274.
European Search Report for EP13178021 dated Sep. 5, 2013.

SALTS OF DASATINIB IN CRYSTALLINE FORM

CROSS-REFERENCE TO RELATED APPLICATIONS

This application is a national stage application (under 35 U.S.C. §371) of PCT/EP2014/065675, filed Jul. 22, 2014, which claims benefit of European Application No. 13178021.5, filed Jul. 25, 2013, both of which are incorporated herein by reference in their entirety.

Dasatinib which is also known as BMS-354825 was disclosed in WO Patent Publication No. 00/62778 and in U.S. Pat. No. 6,596,746. Dasatinib, chemically N-(2-chloro-6-methylphenyl)-2-[[6-[4-(2-hydroxyethyl)-1-piperazinyl]-2-methyl-4-pyrimdinyl]amino]-5-thiazolecarboxamide, is represented by the following structure:

formula 1

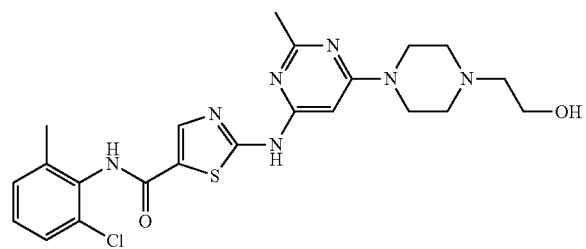

Dasatinib is a drug produced by Bristol-Myers Squibb and sold under the trade name Sprycel® (which contains Dasatinib monohydrate as the active ingredient). Dasatinib is an oral dual BCR/ABL and Src family tyrosine kinase inhibitor approved for use in patients with chronic myelogenous leukemia (CML) after imatinib treatemant and Philadelphia chromo-some-positive acute lymphoblastic leukemia (Ph+ ALL).

The present invention primarily relates to a crystalline substance, preferably a salt of Dasatinib in crystalline form, comprising a compound of formula 1 (cf. above), preferably a cation of a compound of formula 1, and a second pharmaceutically acceptable compound selected from the group consisting of glutaric acid, nicotinic acid and saccharin, preferably an anion thereof.

The invention is further related to pharmaceutical compositions comprising said substance or, preferably, salt. Furthermore, the invention also relates to processes for preparing said substance or, preferably, salt. The invention also relates to several aspects of using said substance or, preferably, salt or pharmaceutical composition to treat a disease. Further details as well as further aspects of the present invention will be described herein below.

Dasatinib is known to exist in close to 60 solid-state forms: a monohydrate, four anhydrous and unsolvated forms which are described in U.S. Pat. No. 7,491,725B2, US2006/0004067A1, U.S. Pat. No. 7,973,045B2, and WO2010/067374, and therein referred to as forms N-6, T1H1-7, B, and I. Further forms (such as 52 solvates) are known from WO2007/035874, US2006/0004067A, WO2009/053854A2, U.S. Pat. No. 8,067,423B, WO2010/062715, and CN102030745. In particular, patent application WO 2010/062715 includes the solvents isosorbide dimethyl ether, N,N'-dimethylethylene urea and N,N'-dimethyl-N,N'-propylene urea. Isosorbide dimethyl ether is used in cosmetic and pharmaceutical formulations.

Some salts of Dasatinib in crystalline form have been described in WO2007/035874.

The discovery of new forms of a pharmaceutically useful compound offers an opportunity to improve the performance profile of a pharmaceutical product. It widens the reservoir of materials a formulation scientist has available for designing a new dosage form of a drug with improved characteristics.

A compound like Dasatinib may give rise to a variety of crystalline forms having distinct crystal structures and physical characteristics like melting point, X-ray diffraction pattern, infrared spectrum, Raman spectrum, and solid state NMR spectrum. One crystalline form may give rise to thermal behavior different from that of another crystalline form. Thermal behavior can be measured in the laboratory by such techniques as capillary melting point, thermogravimetric analysis (TGA), and differential scanning calorimetry (DSC) as well as content of solvent in the crystalline form, which have been used to distinguish polymorphic forms.

There exists a continuing need for providing other solid forms, especially crystalline forms, of N-(2-chloro-6-methylphenyl)-2-[[6-[4-(2-hydroxyethyl)-1-piperazinyl]-2-methyl-4-pyrimidinyl]amino]-5-thiazolecarboxamide. One reason is the highly complex polymorph landscape of said compound and the hereto related difficulties to produce a single and pure crystalline form comprising Dasatinib. Another object is to provide solid forms of Dasatinib to optimize manufacture, formulation, stability, and biological efficiency. Preferably, the new solid forms should show advantages with respect to solubility, lower complexity of their polymorph landscape, in particular a reduced tendency for solvate formation, and/or improved behavior on filtration, drying and crystallization.

According to a preferred objective in connection with the present invention, the new crystalline forms are essentially free of residual solvent.

SUMMARY OF THE INVENTION

The Invention provides novel molecular crystalline substances, preferably salts of Dasatinib in crystalline form, comprising a compound of formula 1 (INN: Dasatinib), preferably a cation of a compound of formula 1, formula 1

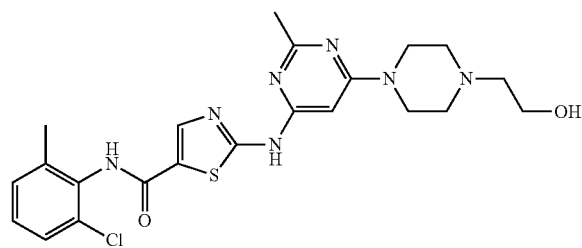

and
a second compound selected from the group consisting of glutaric acid, nicotinic acid and saccharin, preferably an anion thereof. Novel pharmaceutical compositions containing these substances and processes for manufacture of such substances as well as aspects of using said substances or compositions to treat a disease are also described herein.

Since the pKa difference between Dasatinib and the acids described herein (see "second compound") is rather high, it is likely that salts are formed. Therefore, the molecular crystalline substances described herein contain Dasatinib and the second compound within the same crystalline phase (i.e. in the form of a molecular crystal), and are hereinafter mostly referred to as salts.

The substance or, preferably, salt is preferably selected from the group consisting of saccharinate, for example saccharinate hydrate or saccharinate isopropanol solvate, glutarate and nicotinate, wherein, the molar ratio of Dasatinib and the organic acid is in the range of from 2:1 to 1:2, preferably about 1:1.

The new solid forms of the invention are especially advantageous with respect to improved solubility, reduced hygroscopicity and correspondingly improved storage stability, as well as improved preparative behavior such as crystallization and removal of impurities (see below).

A BRIEF DESCRIPTION OF THE FIGURES

Figure 2:
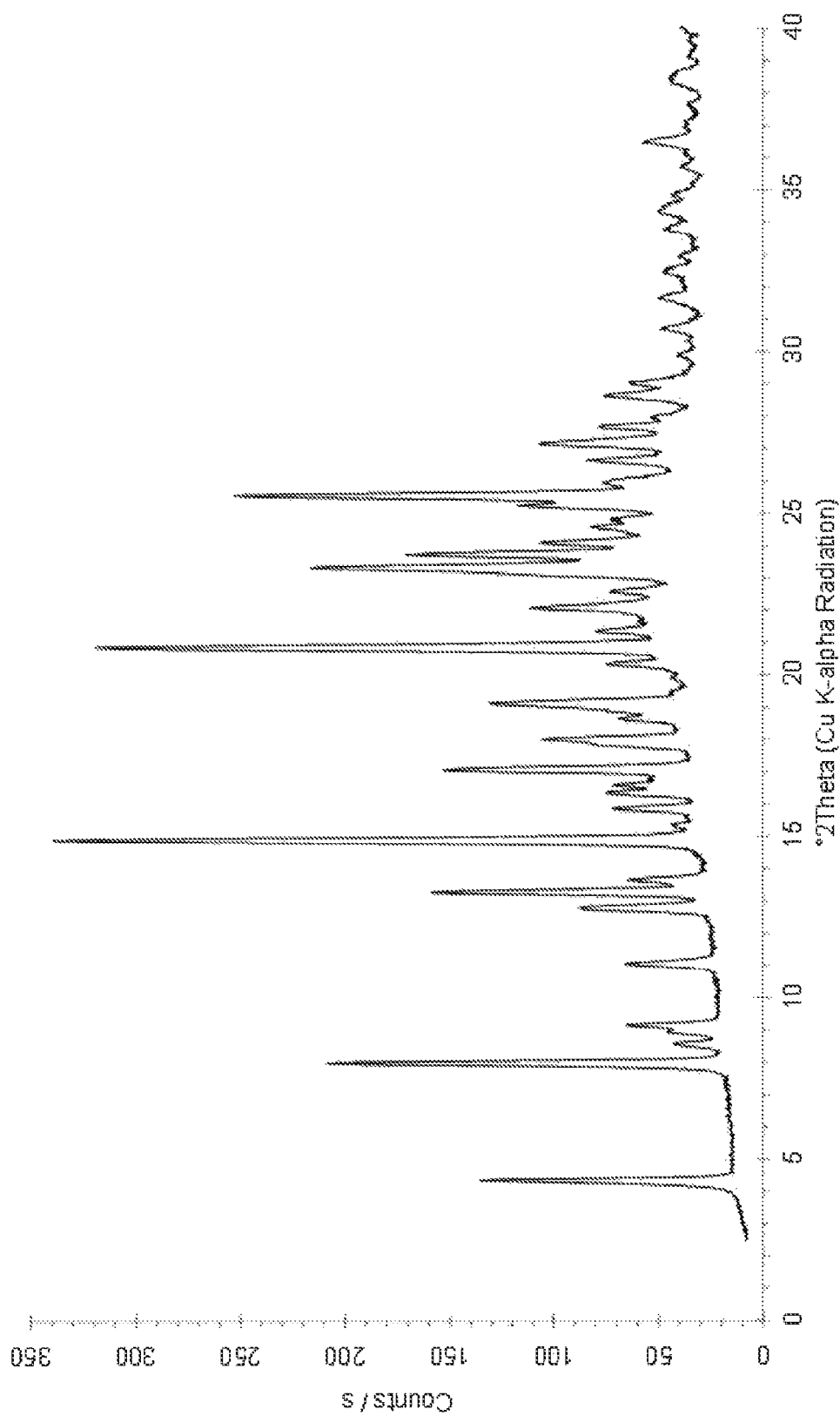
Figure 3:
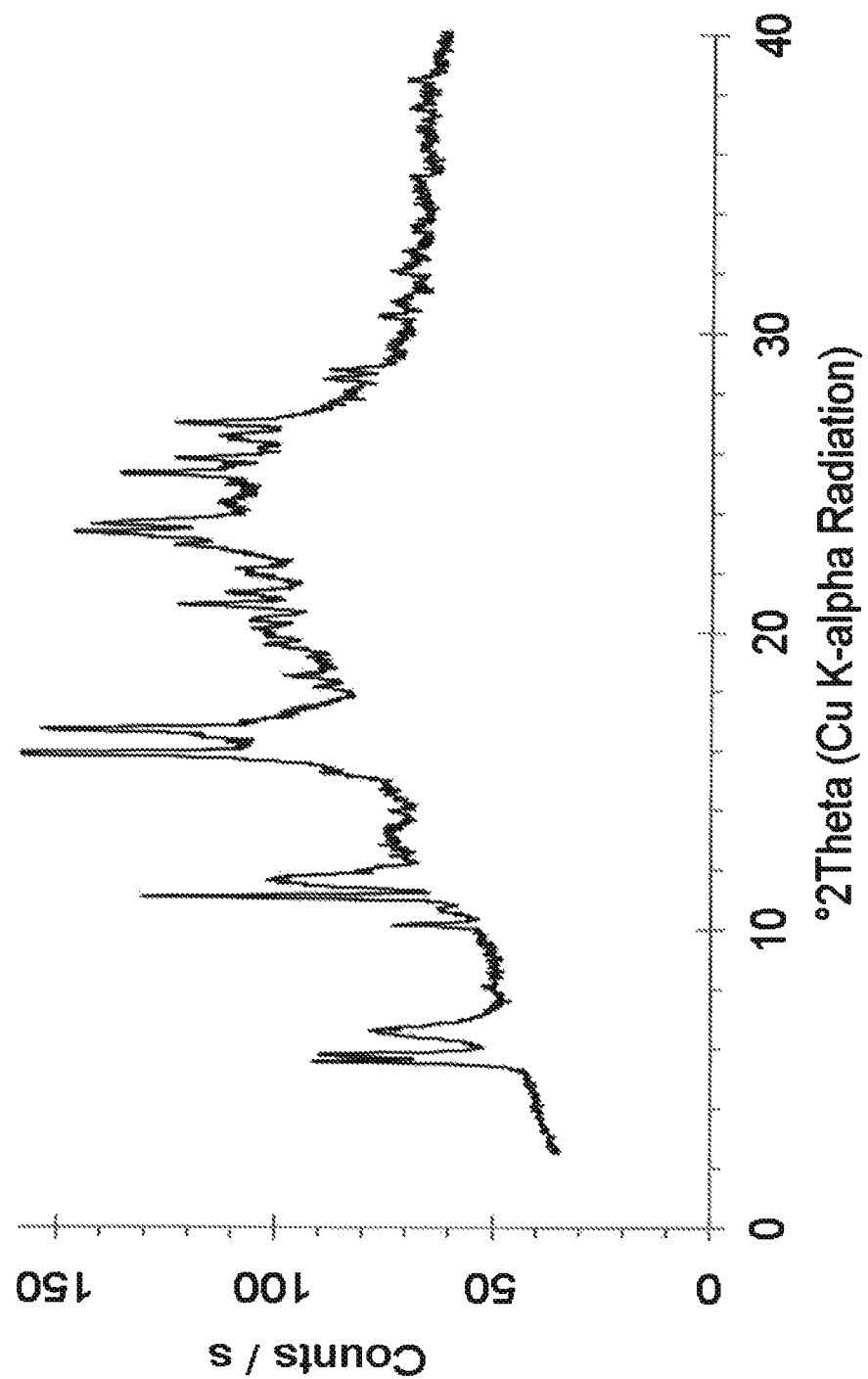
Figure 4:
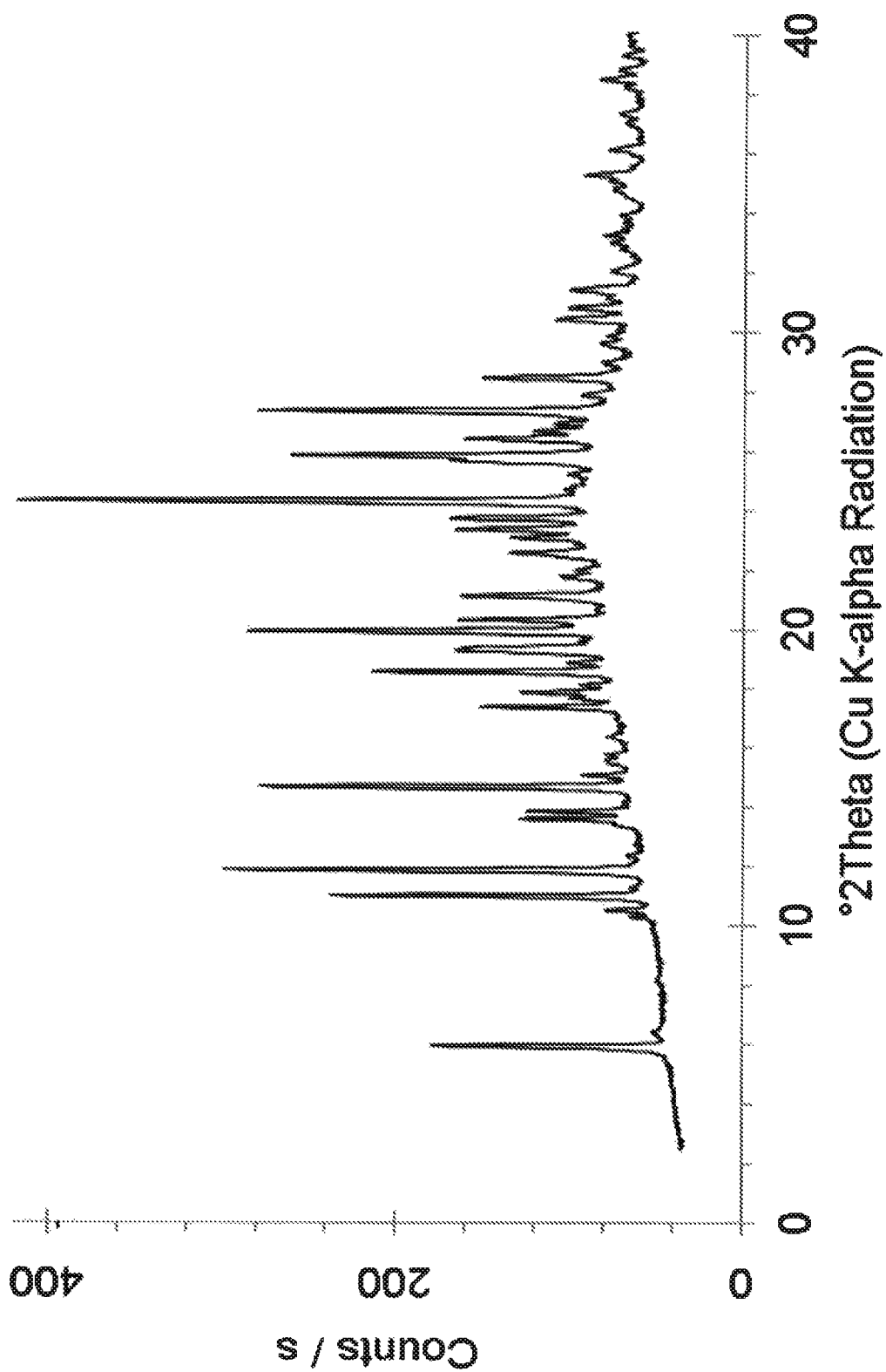
Figure 5:
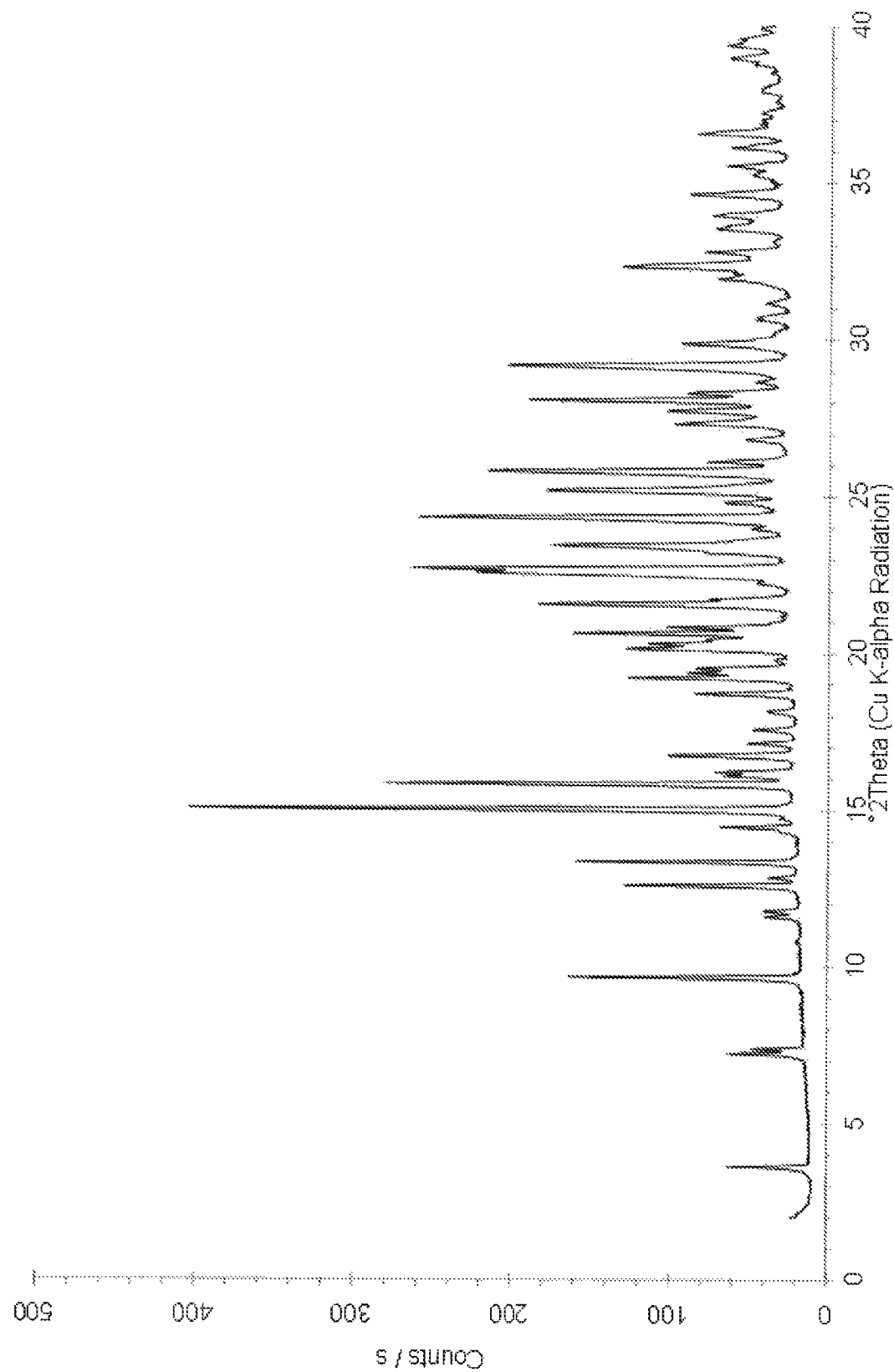

FIG. 1: PXRD pattern of crystalline Dasatinib saccharinate (hydrate) of example 1.
FIG. 2: PXRD pattern of crystalline Dasatinib saccharinate (isopropanol solvate).
FIG. 3: PXRD pattern of crystalline Dasatinib glutarate.
FIG. 4: PXRD pattern of crystalline Dasatinib nicotinate.
FIG. 5: PXRD pattern of crystalline Dasatinib saccharinate (hydrate) of example 5.

DETAILED DESCRIPTION OF THE INVENTION

The present invention is directed to a molecular crystalline substance, preferably a salt of Dasatinib in crystalline form, comprising or consisting of a compound of formula 1 (INN: Dasatinib), preferably a cation of a compound of formula 1,

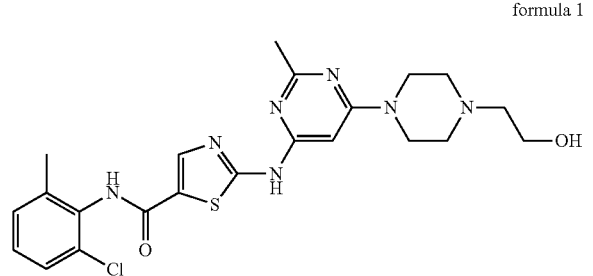 [SMILES: Cc1nc(Nc2ncc(C(=O)Nc3c(C)cccc3Cl)s2)cc(N2CCN(CCO)CC2)n1]

formula 1 and
a second compound selected from the group consisting of glutaric acid, nicotinic acid and saccharin, preferably an anion thereof.

As mentioned above, the substance or, preferably, salt according to the invention is in crystalline form, i.e. the substance or, preferably, salt is preferably substantially free of the amorphous form of Dasatinib or, respectively, does not contain any amorphous Dasatinib at all. Preferably, the substance or, preferably, salt is selected from the group consisting of saccharinate, preferably saccharinate hydrate or saccharinate isopropanol solvate, glutarate and nicotinate.

Preferably, the substance or, preferably, salt is characterized in that the molar ratio of the Dasatinib and the organic acid is in the range of from 2:1 to 1:2, preferably about 1:1.

In a preferred embodiment, the substance or, preferably, salt according to the invention is a glutarate and, respectively, the second compound is glutaric acid. Preferably, such a salt has a PXRD pattern with at least one, preferably more or all characteristic peak(s) (expressed in 2θ±0.2° 2θ (CuKα radiation)) selected from the following peaks located at 5.6, 5.8, 11.1, 15.8, 16.7, 23.3, 23.5 and 25.2°.

In a further preferred embodiment, the substance or, preferably, salt according to the invention is a nicotinate and, respectively, the second compound is nicotinic acid. Preferably, such a salt has a PXRD pattern with at least one, preferably more or all characteristic peak(s) (expressed in 2θ±0.2° 2θ (CuKα radiation)) selected from the following peaks located at 5.9, 11.0, 14.7, 19.9, 24.3, 25.8 and 27.3°.

In a yet further preferred embodiment, the substance or, preferably, salt according to the invention is a saccharinate and, respectively, the second compound is saccharin. Preferably, the substance or, preferably, salt is a saccharinate isopropanol solvate and has a PXRD pattern with at least one, preferably more or all characteristic peak(s) (expressed in 2θ±0.2° 2θ (CuKα radiation)) selected from the following peaks located at 4.3, 8.0, 14.9, 20.8, 23.7 and 25.5°, or a saccharinate hydrate and has a PXRD pattern with at least one, preferably more or all characteristic peak(s) (expressed in 2θ±0.2° 2θ (CuKα radiation)) selected from the following peaks located at 15.1, 20.4, 21.6 and 24.4° or selected from the following peaks located at 9.7, 13.4, 15.1, 20.4, 20.7, 21.6, 22.6, 23.5, 24.4 and 25.2°.

Another object of the invention is a process for obtaining a substance or, preferably, a salt according to the invention (as described herein) comprising the steps of.
a) providing a compound of formula 1 (INN: Dasatinib)

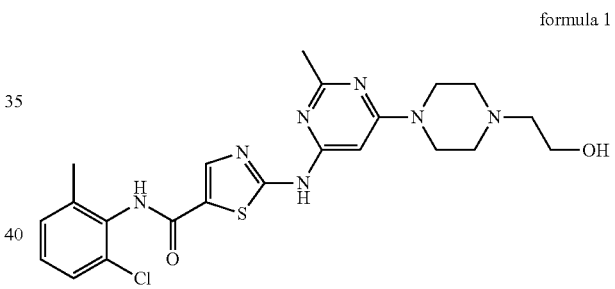

formula 1 in a suitable solvent or a mixture of solvents
b) adding glutaric acid, or nicotinic acid, or, especially, saccharin to the mixture of step a);
c) optionally concentrating the composition of step b);
d) crystallizing;
e) optionally evaporating to dryness or equilibrating the obtained suspension of step d); and
f) isolating the obtained precipitate.

Another object of the Invention is a process for obtaining a substance or, preferably, a salt according to the invention (as described herein) comprising the steps of:
a) providing a compound of the formula 1, which is also known as Dasatinib, in a suitable solvent or a mixture of solvents;
b) adding saccharin to the mixture of step a); and preferably heating the composition to about 60° C.;
c) optionally stirring the composition of step b) at about 60° C. and/or concentrating the composition of step b);
d) cooling the composition of step b) or c) to about 40° C.); optionally seeding the composition; and optionally stirring the composition at about 40° C. for about 1 hour;
e) further cooling the composition of step d) to about 20° C., and stirring at about 20° C.;
f) isolating the obtained precipitate.

Where temperatures are indicated above as conforming "about" to a certain degree, this generally specifies a certain temperature range around the given temperature; thus, "about 60° C." denotes the temperature range 50-80° C., especially 55-70° C.; "about 40° C." denotes the temperature range 30-50° C., especially 35-45° C.; "about 20° C." denotes the temperature range 0-30° C., especially 10-25° C. The time period of "about 1 hour" denotes the range 0.5-2 hours, especially 0.5-1.5 hours. The advantageous seeding step is usually accomplished by addition of 0.1-10% (by weight of the total Dasatinib in the composition), preferably about 1%, of seeding crystals of the desired substance or salt, which has been obtained in a previous crystallization of the same substance.

The crystalline substance or salt of the present invention may be used in pharmaceutical compositions in the same way as other forms of Dasatinib previously known. Additionally, the present crystalline substance or salt may be employed as an intermediate or starting material to produce the pure active ingredient (especially the active ingredient combined with the present second compound, but reduced concentrations of other undesired components), e.g. in form of the crystalline salt. The present invention thus further provides a method for the purification of Dasatinib, which method is characterized by the step of precipitating and/or isolating the crystalline substance, or preferably crystalline salt, of Dasatinib and glutaric acid, nicotinic acid or especially saccharin, e.g. as foreseen by steps d), e) and/or f) of the process for obtaining the crystalline composition described above. This method of the invention preferably employs saccharin as the salt former with Dasatinib for this purpose. The crystalline substance, or preferably crystalline salt, is most preferably of the composition described above, and in the present examples.

The purification process conveniently follows the same steps (a) to (f) as described above for the crystallization of the present crystalline substance or salt. For use as a medicament, the thus obtained product may be employed; if desired, however, the second compound may conveniently be separated again using conventional separation techniques known in the art.

An example is a process comprising the steps of:
a) providing a compound of formula 1 (also known as Dasatinib) in a suitable solvent or a mixture of solvents;
b) adding saccharin to the mixture of step a);
c) heating the composition of step b) to about 60° C.;
d) optionally stirring the composition of step c) at about 60° C.
e) cooling the composition of step c) or d) to about 40° C.);
f) optionally seeding the composition of step e);
g) optionally stirring the composition of step e) or f) at about 40° C. for about 1 hour,
h) cooling the composition of step e), f) or g) to about 20° C.
i) stirring the composition of step h) at about 20° C.
j) isolating the obtained precipitate.

Preferably, the molar ratio of compound of formula 1 (in step a)) and the second compound (glutaric acid, or nicotinic acid, or saccharin) (in step b)) is in the range of from 2:1 to 1:2, preferably about 1:1.

Step b) usually comprises providing glutaric acid, or nicotinic acid, or saccharin in solid form, or as a solution, generally in water, an alcohol, a ketone, an acetate, or a mixture of solvents, preferably in methanol, isopropanol, water or a mixture of suitable solvents.

Preferably, the solvent used in step a) is water or a water miscible organic solvent such as an alcohol (e.g. methanol or especially ethanol) or an aprotic polar organic solvent such as DMSO, DMF, or NMP, or mixtures thereof. Particularly preferred is the use of methanol, ethanol, isopropanol, water or a mixture of suitable solvents.

Solutions or suspension according to steps a) and/or b) preferably are concentrated solutions.

In a further preferred embodiment in step d), e) and/or f) suitable seed crystals are added.

The concentration of Dasatinib in step a) may range from 0.1 to about 1000 mg/ml of solvents, preferably from 5 to 300 mg/ml. The concentration of glutaric acid, or nicotinic acid, or saccharin in step b) may range from 0.1 to about 500 mg/ml of solvents, preferably from 5 to 200 mg/ml.

The process is preferably carried out in the temperature range from 15-120° C. In a preferred process, steps a), b) and/or c) are carried out at a temperature in the range from 20-90° C. Preferably, the suspension is tempered and then cooled before the isolation step is carried out.

Optionally, the solvent from the suspension is completely evaporated before isolation.

In a preferred process, the crystalline composition is isolated by filtering off the crystals and drying, e.g. in vacuum, an inert gas flow or both at ambient temperature, or elevated temperatures up to about 90° C.

Ambient temperature is preferably meant to be room temperature, being preferably 20 to 30° C. and most preferably 20 to 25° C.

The substances or, preferably, salts of the present invention are generally obtained as a fine powder with typical particle size distributions with the median size between 0.1 and 100 µm, preferably between 1 and 50 µm, preferably between 1 to 10 µm. This particle size range ensures a fast dissolution profile, while retaining the favorable handling properties in the formulation process.

The substance or, preferably, salts of the present invention may be used in pharmaceutical compositions in the same way as other forms of Dasatinib previously known. Additionally, the present substances or salts may be employed as intermediates or starting materials to produce the pure active ingredient.

A further aspect of the present invention is a pharmaceutical composition comprising, as active ingredient, a substance or, preferably, a salt according to the present invention, preferably a salt as described herein above as being preferred, and preferably further comprising one, two, three, or more pharmaceutically acceptable carriers, and/or diluents, and/or further ingredients, in particular one, two, three, or more pharmaceutical excipients.

The amount of the substance or, preferably, salt in the composition depends on the type of formulation and the desired dosage regimen during administration time periods. The amount in each oral formulation may be from 0.1 to 300 mg, preferably from 1.0 to 250 mg, in particular from 5.0 to 200 mg.

Oral formulations (as preferred pharmaceutical compositions according to the present invention) may be solid formulations such as capsules, tablets, pills and troches, or a liquid suspension formulation.

The substances or, preferably, salts according to the invention may be used directly in the form of powders, granules, suspensions, or they may be combined together with other pharmaceutically acceptable ingredients in admixing the components and optionally finely divide them, and then filling capsules, composed for example from hard or soft gelatin, compressing tablets, pills or troches, or suspend in suspensions. Coatings may be applied after compression to form pills.

Pharmaceutically acceptable ingredients are well known for the various types of formulation and may be for example binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Examples for binders are gum tragacanth, acacia, starch, gelatin, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated poly-acrylamides, poly-maleic acid and esters or -amides thereof, poly-acrylic acid and esters or -amides thereof, poly-vinylalcohol und esters or -ethers thereof, poly-vinylimidazole, poly-vi-nylpyrrolidon, und natural polymers like chitosan, carragenan or hyaluronic acid.

Examples for excipients are phosphates such as dicalcium phosphate.

Examples for disintegrants are croscarmellose sodium, crospovidone, low-substituted hydroxypropyl cellulose, sodium starch glycolate or alginic acid.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctyl-sulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatin, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for solid carriers are talc, clay, microcrystalline cellulose, silica, alumina and the like.

The formulation according to the invention may also contain isotonic agents, such as sugars, buffers or sodium chloride.

The compositions of the present invention may also be formulated as effervescent tablet or powder, which can disintegrate in an aqueous environment to provide a drinking solution.

The most preferred route is oral administration. The dosages may be conveniently presented in a unit dosage form and prepared by any of the methods well-known in the art of pharmacy.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropyl-methyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The substances or, preferably, salts of the present invention and its formulations or compositions containing the same, respectively, can be also administered in combination with other therapeutic agents being effective to treat a given condition and/or to provide a combination therapy.

The substances or, preferably, salts of the present invention and the pharmaceutical compositions according to the invention are useful for effective treatment of disorders in connection with need of inhibiting the BCR/ABL and Src family tyrosine kinases. The substances or, preferably, salts of the present invention and the respective pharmaceutical compositions are useful in the treatment of chronic myelogenous leukemia but also advanced prostate cancer.

The substances or, preferably, salts of the present invention and the pharmaceutical compositions according to the invention can also be used in a therapeutic method for producing an Abl tyrosine kinase inhibiting effect in a mammal comprising administering to a mammal in need of such therapy.

The substances or, preferably, salts of the present invention may be used as single component or as mixtures with other solid forms.

In view of the above, the present invention also relates to substances or, preferably, salts of the present invention and pharmaceutical compositions according to the invention for use as a medicament, preferably for use in the treatment of cancer, in particular of chronic myelogenous leukemia (CML) and/or Philadelphia chromosome-positive acute lymphoblastic leukemia (Ph+ALL).

In the following, the present invention will be described more closely by way of selected examples illustrating the invention. Wherever noted, in the following, room temperature depicts a temperature from the range 22-25° C. and percentages are given by weight, if not indicated otherwise.

ABBREVIATIONS

DSC differential scanning calorimetry
DVS dynamic vapor sorption
HPLC high pressure liquid chromatography
DMSO dimethyl sulfoxide
NMR nuclear magnetic resonance
TG-FTIR thermogravimetry coupled with Fourier-transformation infrared spectrometry
r.h. relative humidity (air, if not indicated otherwise)

TGA thermogravimetry
v/v volume by volume
PXRD powder X-ray diffraction
Instrumental:
Powder X-Ray Diffraction:

The measurements were carried out with a Bruker D8 Advance powder X-ray diffractometer using Cu Kα radiation in the Bragg-Brentano reflection geometry. Generally, the 2θ values are accurate within an error of ±0.1-0.2° and comparable with results from other determinations, where a comparable instrument and sample preparation method has been used. The relative peak intensities can vary considerably for different samples of the same crystalline form because of different preferred orientations of the crystals. The samples were prepared without any special treatment other than the application of slight pressure to get a flat surface. Generally, silicon single crystal sample holders of 0.1 mm, 0.5 mm or 1.0 mm depth were used. The tube voltage and current were 40 kV and 40 mA, respectively. The X-ray diffractometer is equipped with a LynxEye detector. A variable divergence slight was used with a 3° window. The step size was 0.02° 2θ with a step time of 37 seconds. The samples were rotated at 0.5 rps during the measurement.
Thermogravimetry coupled to infrared spectroscopy (TG-FTIR):

Thermogravimetry coupled with FT-infrared spectroscopy is a well known method that allows to monitor the mass loss of a given sample upon heating while identifying the volatile substances by infrared spectroscopy. Therefore, TG-FTIR is a suitable method to identify solvates or hydrates.

TG-FTIR was performed on a Netzsch Thermo-Microbalance TG 209, which is coupled to a Bruker FT-IR Spectrometer Vector 22 or IFS 28. The measurements were carried out with aluminum crucibles with a micro pinhole under a nitrogen atmosphere and at a heating rate of 10° C./min over the range 25-250° C.

$^1$H-NMR: The $^1$H-NMR spectra were recorded on a Bruker DPX 300 spectrometer. Solvent Deuterated-DMSO Differential scanning calorimetry: DSC is carried out with a TA Instruments DSC Q2000 using hermetically sealed gold sample pans. The heating rate is 10° C. per minute.

Dynamic vapor sorption: DVS is performed at 25° C. with an SPS11-100n "Sorptions Prüfsystem" of Projekt Messtechnik, D-89077 Ulm (Germany). About 25 mg of sample is put into an aluminum sample pan. Humidity program: 50% relative humidity (r.h.) for 2 hours, 50% r.h. to 95% r.h. (humidity change rate 5% per hour), 95% r.h. for 5 hours, 95% r.h. to 50% r.h. (humidity change rate 5% per hour), 50% r.h. for 2 hours.

High pressure liquid chromatography: HPLC is carried out on an Agilent 1100 HPLC chromatograph equipped with a UV-vis detection unit. The column type used is a Waters XTerra MS C18, 250×4.6 mm, 5 μm (FK-CC14B). The method is an isocratic method using aqueous ammonium acetate/acetic acid and methanol with a ratio of 55/45. The applied flow rate was 1.0 mL per minute, the injection volume is 20 microliter and the detection wavelength is 321 nm.

Solvents: For all experiments, standard grade solvents are used.

EXAMPLES

Example 1

Preparation of Crystalline Dasatinib Saccharinate (Hydrate)

126 mg of Dasatinib (monohydrate form) and 46 mg of saccharin are suspended in 5 mL of water. The suspension is heated to 70° C. and stirred at 70° C. for 45 minutes. The mixture is allowed to cool to room temperature and stirred for 6 days at room temperature. Each day during the duration of the experiment the mixture is subjected to sonication for about one minute in a common ultrasonic bath. After six days of stirring the obtained suspension is filtered and air dried at room temperature. After drying at room temperature, the obtained solid product is characterized by powder X-ray diffraction and a PXRD pattern similar to that shown in FIG. 1 showing peaks at locations as presented in Table 1 is obtained. The product is further dried at about 60° C./30 mbar for 1 hour and H-NMR spectroscopy, TG-FTIR and powder X-ray diffraction is performed. H-NMR indicates a molar ratio of Dasatinib to saccharin of 1:1 and the PXRD pattern as shown in FIG. 1 showing peaks at locations as presented in Table 1 is obtained. TG-FTIR reveals a mass loss of about 2.3% which is attributable to loss of water, so as to it can be assumed that the solid material is a crystalline hydrate.

TABLE 1

2-theta angles, d-spacings and qualitative relative intensities for dasatinib saccharinate hydrate.

| Angle °2θ | d value [Å] | Qualitative relative intensity |
|---|---|---|
| 3.7 | 23.8 | vw |
| 7.3 | 12.1 | vw |
| 7.5 | 11.9 | vw |
| 9.7 | 9.1 | m |
| 11.7 | 7.5 | w |
| 11.9 | 7.5 | w |
| 12.7 | 7.0 | w |
| 13.4 | 6.6 | m |
| 15.1 | 5.87 | vs |
| 15.9 | 5.57 | m |
| 16.2 | 5.46 | m |
| 16.8 | 5.27 | m |
| 18.8 | 4.72 | m |
| 19.4 | 4.58 | m |
| 20.4 | 4.36 | vs |
| 20.7 | 4.29 | s |
| 20.9 | 4.25 | m |
| 21.6 | 4.11 | vs |
| 22.6 | 3.93 | vs |
| 23.5 | 3.78 | vs |
| 24.4 | 3.65 | vs |
| 24.9 | 3.58 | m |
| 25.2 | 3.52 | vs |
| 25.8 | 3.45 | s |
| 28.1 | 3.17 | s | vs = very strong,
s = strong,
m = medium,
w = weak

Example 2

Preparation of Crystalline Dasatinib Saccharinate (Isopropanol Solvate)

126 mg of Dasatinib (monohydrate form) and 46 mg of saccharin are suspended in 3 mL of isopropanol. The suspension is heated to 70° C. and stirred at 70° C. for 45 minutes. The suspension is allowed to cool to room temperature and stirred for 16 hours at room temperature, sonicated for 1 minute, again stirred for 3 hours at room temperature. After filtration and drying in air at room temperature the solid product is characterized PXRD, TG-FTIR and H-NMR spectroscopy. H-NMR spectroscopy indicates a molar ratio of Dasatinib to saccharin of 1:1. TG-FTIR reveals a mass loss of about 15% which is attributable to loss of isopropanol, so as to it can be assumed that the solid material is an isopropanol solvate. The obtained PXRD pattern which is shown in FIG. 2 shows peaks at locations as presented in Table 2.

TABLE 2

2-theta angles, d-spacings and qualitative relative intensities for Dasatinib sacharinate isopropanol solvate.

| Angle °2θ | d value [Å] | Qualitative relative intensity |
|---|---|---|
| 4.3 | 20.3 | m |
| 8.0 | 11.1 | s |
| 8.6 | 10.3 | vw |
| 9.1 | 9.7 | w |
| 11.0 | 8.0 | w |
| 12.8 | 6.9 | w |
| 13.3 | 6.7 | s |
| 13.6 | 6.5 | w |
| 14.9 | 5.95 | vs |
| 15.8 | 5.59 | w |
| 16.3 | 5.42 | w |
| 17.0 | 5.20 | s |
| 18.0 | 4.92 | m |
| 18.6 | 4.76 | w |
| 19.1 | 4.64 | m |
| 20.8 | 4.26 | vs |
| 21.3 | 4.16 | w |
| 22.0 | 4.03 | m |
| 22.6 | 3.94 | w |
| 23.3 | 3.82 | s |
| 23.7 | 3.75 | s |
| 24.1 | 3.69 | m |
| 25.2 | 3.53 | m |
| 25.5 | 3.49 | vs |
| 27.1 | 3.28 | m | vs = very strong,
s = strong,
m = medium,
w = weak

Example 3

Preparation of Crystalline Dasatinib Glutarate 127 mg of Dasatinib (monohydrate form) and 34 mg of glutaric acid are dissolved in 10 mL of methanol at 60° C. and stirred for 0.5 hour at 60° C. The solvent is evaporated using a dry nitrogen flow at 60° C. within approximately 2.5 hours and the dried sample is held at 60° C. for 1 hour. The sample is cooled and stored overnight at room temperature. H-NMR spectroscopy indicates a molar ratio of Dasatinib to glutaric acid of about 1:1. The solid material is further characterized by powder X-ray diffraction. The obtained PXRD pattern which is shown in FIG. 3 exhibits sharp peaks. The peak locations of the PXRD pattern are listed in Table 3.

TABLE 3

2-theta angles, d-spacings and qualitative relative intensities for Dasatinib glutarate.

| Angle °2θ | d value [Å] | Qualitative relative intensity |
|---|---|---|
| 5.6 | 15.9 | m |
| 5.8 | 15.3 | m |
| 6.6 | 13.5 | w |
| 10.1 | 8.7 | w |
| 11.1 | 8.0 | m |
| 11.6 | 7.6 | m |
| 15.8 | 5.59 | vs |

TABLE 3-continued 2-theta angles, d-spacings and qualitative relative intensities for Dasatinib glutarate.

| Angle °2θ | d value [Å] | Qualitative relative intensity |
|---|---|---|
| 16.7 | 5.31 | s |
| 20.9 | 4.26 | m |
| 21.3 | 4.18 | m |
| 23.3 | 3.82 | s |
| 23.5 | 3.78 | s |
| 25.2 | 3.53 | s |
| 25.7 | 3.46 | m |
| 26.9 | 3.31 | m |
| 28.4 | 3.14 | m |
| 28.7 | 3.11 | m | vs = very strong,
s = strong,
m = medium,
w = weak

Example 4

Preparation of Crystalline Dasatinib Nicotinate 127 mg of Dasatinib (monohydrate form) and 31 mg of nicotinic acid are dissolved in 10 mL of methanol at 60° C. and stirred for 0.5 hour at 60° C. The solvent is evaporated using a dry nitrogen flow at 60° C. within approximately 2.5 hours and the dried sample is held at 60° C. for 1 hour. The sample is cooled and stored overnight at room temperature. H-NMR spectroscopy indicates a molar ratio of Dasatinib to nicotinic acid of 1:1. The solid material is further characterized by powder X-ray diffraction. The obtained PXRD pattern which is shown in the FIG. 4 exhibits sharp peaks. The peak locations of the PXRD pattern are listed in Table 4.

TABLE 4

2-theta angles, d-spacings and qualitative relative intensities for Dasatinib nicotinate.

| Angle °2θ | d value [Å] | Qualitative relative intensity |
|---|---|---|
| 5.9 | 14.9 | m |
| 10.3 | 8.6 | vw |
| 10.5 | 8.4 | vw |
| 11.0 | 8.0 | m |
| 11.9 | 7.5 | s |
| 13.6 | 6.5 | w |
| 13.8 | 6.4 | w |
| 14.7 | 6.0 | s |
| 15.1 | 5.88 | w |
| 17.3 | 5.11 | w |
| 17.6 | 5.03 | w |
| 17.8 | 4.97 | w |
| 18.1 | 4.90 | w |
| 18.5 | 4.78 | m |
| 18.8 | 4.71 | w |
| 19.3 | 4.59 | m |
| 19.9 | 4.46 | s |
| 20.3 | 4.38 | m |
| 21.1 | 4.21 | m |
| 21.7 | 4.08 | w |
| 22.5 | 3.94 | w |
| 23.0 | 3.86 | w |
| 23.3 | 3.81 | m |
| 23.7 | 3.75 | m |
| 24.3 | 3.67 | vs |
| 25.2 | 3.54 | w |
| 25.6 | 3.47 | m |
| 25.8 | 3.45 | s |
| 26.4 | 3.38 | m |

TABLE 4-continued 2-theta angles, d-spacings and qualitative relative intensities for Dasatinib nicotinate.

| Angle °2θ | d value [Å] | Qualitative relative intensity |
|---|---|---|
| 26.6 | 3.34 | w |
| 26.9 | 3.31 | w |
| 27.3 | 3.26 | s |
| 27.8 | 3.20 | w |
| 28.4 | 3.14 | m | vs = very strong,
s = strong,
m = medium,
w = weak

Example 5

Preparation of Crystalline Dasatinib Saccharinate (Hydrate)

30.34 g of dasatinib (monohydrate form) and 11.43 g of saccharin are suspended in 800 mL of ethanol/water 30:70 v/v at room temperature. The suspension is stirred using a paddle stirrer, heated to 60° C. and stirred at 60° C. until complete dissolution. The solution is then cooled to 40° C. in approx. 1 hour and seeded with a sonicated suspension containing about 0.42 g of crystalline dasatinib saccharinate salt (monohydrate) in 6 mL of ethanol/water 30:70 v/v. The weak suspension formed is stirred at 40° C. for 0.5 hour and cooled to 35° C. in 1 hour. The suspension is seeded again with a sonicated suspension containing 0.43 g of crystalline dasatinib saccharinate salt (monohydrate) in 6 mL of ethanol/water 30:70 v/v and cooled to 22° C. at a cooling rate of 5K/hour. The suspension is stirred at 22° C. for 16 hours and filtered. The suspension is easy to transfer into the filter device and easy to filter. The solid material is washed with 200 mL of ethanol/water 30:70 v/v. The solid material is then air dried at room temperature for approx. 20 minutes, further dried in a vacuum dryer at room temperature/approx. 30 mbar for 15 minutes, heated to 80° C. in about 1 hour and dried at 80° C./approx. 30 mbar for about 2 hours. Yield: 33.9 g. H-NMR spectroscopy, DSC, DVS, HPLC and powder X-ray diffraction is performed. H-NMR indicates a molar ratio of Dasatinib to saccharin of A1 1:1 and the PXRD pattern as shown in Fig 5. DSC shows an endothermal peak with an onset temperature of about 140° C. The HPLC purity of sample is 100% (area %). The crystallization process eliminated the weak impurity (about 0.05 area %) present in the starting material of dasatinib hydrate. DVS shows that the material is not hygroscopic.

The invention claimed is:

1. A molecular crystalline substance in crystalline form, comprising a compound of formula 1 also known as Dasatinib, formula 1

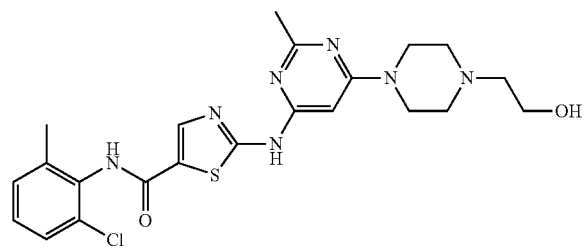

and
a second compound selected from the group consisting of
a) saccharin which crystalline substance has a PXRD pattern with at least one characteristic peak, expressed in 2θ±0.2° 2θ using CuKα radiation, selected from the following peaks located at 9.7, 13.4, 15.1, 20.4, 20.7, 21.6, 22.6, 23.5, 24.4 and 25.2° or a PXRD pattern with at least one characteristic peak, expressed in 2θ±0.2° 2θ using CuKα radiation, selected from the following peaks located 4.3, 8.0, 14.9. 20.8, 23.7 and 25.5°,
b) glutaric acid which crystalline substance has a PXRD pattern with at least one characteristic peak, expressed in 2θ±0.2° 2θ using CuKα radiation, selected from the following peaks located at 5.6, 5.8, 11.1, 15.8, 16.7, 23.3, 23.5 and 25.2°, and
c) nicotinic acid which crystalline substance has a PXRD pattern with at least one characteristic peak, expressed in 2θ±0.2° 2θ using CuKα radiation, selected from the following peaks located at 5.9, 11.0, 14.7, 19.9, 24.3, 25.8 and 27.3°.

2. The substance according to claim 1, wherein the substance is a saccharinate salt.

3. The substance according to claim 1, wherein the substance is a salt selected from the group consisting of saccharinate hydrate, saccharinate isopropanol solvate, glutarate and nicotinate.

4. The substance as claimed in claim 1, wherein the molar ratio of Dasatinib and the organic acid is in the range of from 2:1 to 1:2.

5. A pharmaceutical composition comprising, as active ingredient, the substance according to claim 1, and further comprising one, two, three, or more pharmaceutically acceptable carriers, diluents, or further ingredients.

6. The pharmaceutical composition according to claim 5, wherein the total amount of the substance in the composition is in the range of from 0.1 to 300 mg.

7. The pharmaceutical composition according to claim 5, wherein the total amount of the substance in the composition is in the range of from 5.0 to 200 mg.

8. A method for treating cancer which comprises administering to a patient in need of treatment an effective amount of the substance as claimed in claim 1.

9. A process for obtaining the substance according to claim 1 comprising the steps of:
a) providing a compound of formula 1, which is also known as Dasatinib, formula 1

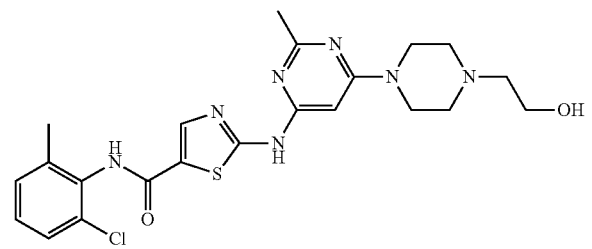

in a solvent or a mixture of solvents
b) adding glutaric acid, or nicotinic acid, or saccharin to the mixture of step a);
c) optionally concentrating the composition of step b);
d) crystallizing;
e) optionally evaporating to dryness or equilibrating the obtained suspension of step d); and
f) isolating the obtained precipitate.

10. A process for the purification of Dasatinib, which is a compound of formula 1,

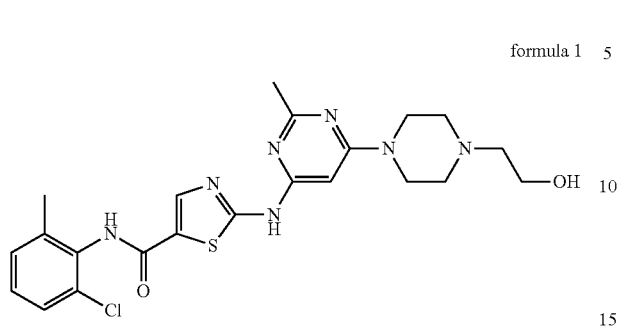

formula 1 which process comprises the steps of providing a solution or dispersion containing the compound of formula 1 and a second compound selected from the group consisting of glutaric acid, nicotinic acid and saccharin in a suitable solvent, and isolating the crystalline substance according to claim 1.

11. A process for the purification of Dasatinib, which is a compound of formula 1,

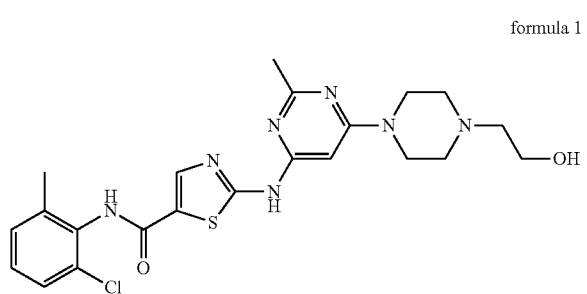 [SMILES: Cc1nc(Nc2ncc(C(=O)Nc3c(C)cccc3Cl)s2)cc(N2CCN(CCO)CC2)n1]

formula 1 which process comprises the steps of providing a solution or dispersion containing the compound of formula 1 and a second compound selected from the group consisting of glutaric acid, nicotinic acid and saccharin in a suitable solvent, and isolating a crystalline substance comprising a compound of formula 1,

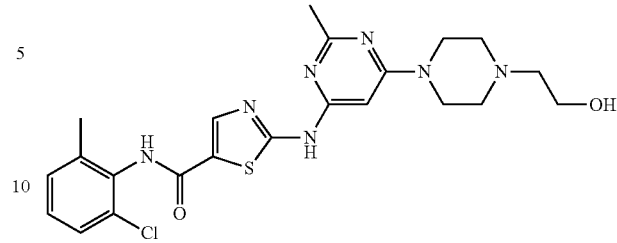

formula 1 and a second compound selected from the group consisting of saccharin, glutaric acid, and nicotinic acid, and said process following the steps (a) to (f) according to claim 9.

12. The process according to claim 11, wherein the second compound is saccharin, and the molar ratio of the compound of formula 1 and saccharin provided is in the range from 1:0.5 to 1:3.

13. The process according to claim 11, wherein the solvent is selected from the group consisting of $C_1$-$C_4$ alcohols, water, or mixtures thereof, and/or wherein seed crystals are added before crystallizing.

14. The pharmaceutical composition according to claim 1, wherein the further ingredients-are one, two, three, or more pharmaceutical excipients.

15. The method for treating cancer as claimed in claim 8, wherein the cancer is chronic myelogenous leukemia or Philadelphia chromosome-positive acute lymphoblastic leukemia.

16. A method for treating cancer which comprises administering to a patient in need of treatment an effective amount of the pharmaceutical composition according to claim 5 to a patient.

17. The method for treating cancer as claimed in claim 15, wherein the cancer is chronic myelogenous leukemia or Philadelphia chromosome-positive acute lymphoblastic leukemia.

18. The method according to claim 8, wherein the total amount of the substance is in the range of from 0.1 to 300 mg.

19. The method according to claim 16, wherein the total amount of the pharmaceutical composition is in the range of from 0.1 to 300 mg.

* * * * *